(12) United States Patent
Hwang et al.

(10) Patent No.: US 11,000,259 B2
(45) Date of Patent: May 11, 2021

(54) ULTRASONIC PROBE

(71) Applicant: SAMSUNG MEDISON CO., LTD., Gangwon-do (KR)

(72) Inventors: Won Soon Hwang, Hanam-si (KR); Jae Yk Kim, Seongnam-si (KR); Gil-Ju Jin, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 396 days.

(21) Appl. No.: 15/868,679

(22) Filed: Jan. 11, 2018

(65) Prior Publication Data

US 2019/0159758 A1   May 30, 2019

(30) Foreign Application Priority Data

Nov. 29, 2017   (KR) .................. 10-2017-0162159

(51) Int. Cl.
| | | |
|---|---|---|
| *A61B 8/00* | (2006.01) | |
| *G01S 7/52* | (2006.01) | |
| *G01S 15/89* | (2006.01) | |
| *A61B 8/08* | (2006.01) | |

(52) U.S. Cl.
CPC .......... *A61B 8/4461* (2013.01); *A61B 8/4405* (2013.01); *A61B 8/4444* (2013.01); *A61B 8/4455* (2013.01); *A61B 8/4483* (2013.01); *G01S 7/52079* (2013.01); *A61B 8/4272* (2013.01); *A61B 8/4411* (2013.01); *A61B 8/464* (2013.01); *A61B 8/483* (2013.01); *A61B 2562/18* (2013.01); *G01S 15/8993* (2013.01)

(58) Field of Classification Search
CPC ..... A61B 8/4461; A61B 8/444; A61B 8/4455; A61B 8/4405; A61B 8/4483; A61B 8/4272; A61B 2562/18; A61B 8/4411; A61B 8/464; A61B 8/483; G01S 7/52079; G01S 15/8993
See application file for complete search history.

(56) References Cited

U.S. PATENT DOCUMENTS

| | | | | |
|---|---|---|---|---|
| 5,531,119 A | * | 7/1996 | Meyers | ................ A61B 8/4281 367/140 |
| 2002/0148277 A1 | * | 10/2002 | Umeda | .................... A61B 8/12 73/1.82 |
| 2008/0194961 A1 | | 8/2008 | Randall | |

(Continued)

FOREIGN PATENT DOCUMENTS

| | | | |
|---|---|---|---|
| JP | 2001-178727 | * | 7/2001 |
| JP | 2001-178727 A | | 7/2001 |

(Continued)

OTHER PUBLICATIONS

Extended European Search Report dated Oct. 1, 2018 issued in European Patent Application No. 18151882.0.

*Primary Examiner* — Sanjay Cattungal

(74) *Attorney, Agent, or Firm* — Morgan, Lewis & Bockius LLP

(57) ABSTRACT

Disclosed herein is an ultrasonic probe for acquiring an ultrasound image. The ultrasound probe includes a transducer configured to be movable, a cap configured to transmit an ultrasound signal generated by the transducer to outside, and an impact mitigating member disposed along a circumference of the cap to protect the cap from an external impact.

20 Claims, 17 Drawing Sheets

(56) References Cited

U.S. PATENT DOCUMENTS

| | | | |
|---|---|---|---|
| 2010/0154547 A1* | 6/2010 | Fukada | B06B 1/0292 |
| | | | 73/632 |
| 2011/0125025 A1* | 5/2011 | Hart | A61B 8/00 |
| | | | 600/459 |
| 2013/0172751 A1* | 7/2013 | Heinrich | A61B 8/4483 |
| | | | 600/444 |
| 2016/0338669 A1* | 11/2016 | Naka | A61B 8/4272 |
| 2017/0112469 A1 | 4/2017 | Song et al. | |
| 2017/0143302 A1* | 5/2017 | Nakanishi | A61B 8/4209 |

FOREIGN PATENT DOCUMENTS

| | | |
|---|---|---|
| JP | 2006-212287 A | 8/2006 |
| JP | 2012-085723 A | 5/2012 |
| JP | 2015-154807 A | 8/2015 |
| KR | 10-2017-0049650 A | 5/2017 |

* cited by examiner

ULTRASONIC PROBE

CROSS-REFERENCE TO RELATED APPLICATION

This application claims the benefit of Korean Patent Application No. 10-2017-0162159, filed on Nov. 29, 2017 in the Korean Intellectual Property Office, the disclosure of which is incorporated herein by reference.

BACKGROUND

1. Field

Embodiments of the present disclosure relate to an ultrasonic probe for acquiring an ultrasound image.

2. Description of the Related Art

An ultrasound imaging device is a device that irradiates an ultrasound signal toward a target site in a subject's body from a surface of the subject's body and uses information on a reflected ultrasound signal (an ultrasound echo signal) to non-invasively obtain an image related to a tomogram of a soft tissue or an image of a blood flow.

In comparison to other imaging diagnostic devices such as an X-ray diagnostic device, an X-ray computerized tomography (CT) scanner, a magnetic resonance imaging (MRI) device, and a nuclear medicine diagnostic device, an ultrasound imaging device has advantages of having a smaller size, being less expensive, being capable of displaying an image in real time, and being safe due to not causing exposure to radiation and the like.

Consequently, the ultrasound imaging is widely used for cardiac diagnosing, abdomen diagnosing, urological diagnosing, and obstetric diagnosing.

Generally, an ultrasound imaging device may include a main body and a probe configured to transmit an ultrasound signal to a subject to be diagnosed and receive a signal reflected from the subject.

The probe may have a structure in which an ultrasound signal transmitted from a transducer therein passes through a cap coming in contact with a subject to be transmitted to the subject, and a returning ultrasound signal reflected from the subject passes through the cap to be received by the transducer.

Because the cap may be mainly formed of elastic rubber (RTV, room temperature vulcanizing silicone rubber), thermoplastic elastomers (TPE), or plastic (synthetic resin or the like), the cap may be vulnerable to external impact and may require caution when being used by a user.

Although a cap formed of rubber or TPE is not easily broken, due to having poor physical properties, an impact may be immediately transmitted to a transducer accommodated inside the cap when the cap receives the impact. Therefore, a separate device for mitigating an impact on the transducer may be required.

When a cap is formed of plastic, the cap itself may become damaged when a predetermined amount of impact is applied thereto. Therefore, to prevent this, the cap should be designed to have a large thickness.

However, designing a cap that has a thickness sufficient for withstanding an impact transmitted from the outside is limited by the need to facilitate the transmission and reception of an ultrasound signal.

SUMMARY

Therefore, it is an aspect of the present disclosure to provide an improved ultrasonic probe that prevents a cap from being damaged by an external impact.

It is another aspect of the present disclosure to provide an improved ultrasonic probe that prevents internal components of a cap from being damaged by an external impact.

It is still another aspect of the present disclosure to provide an improved ultrasonic probe that includes an impact mitigating member disposed along a circumference of a cap.

Additional aspects of the disclosure will be set forth in part in the description which follows and, in part, will be obvious from the description, or may be learned by practice of the disclosure.

In accordance with one aspect of the present disclosure, an ultrasonic probe includes a transducer configured to be movable, a cap configured to transmit an ultrasound signal generated by the transducer to outside, and an impact mitigating member disposed along a circumference of the cap to protect the cap from an external impact.

The impact mitigating member may have elasticity to be deformed by an external impact and be returned to its original state when the external impact is removed.

The impact mitigating member may include a first impact mitigating member having elasticity to mitigate an impact transmitted to the cap from outside.

The cap may include an upper cap configured to come in contact with an external subject and transmit the ultrasound signal generated by the transducer to the external subject and a lower cap disposed below the upper cap, and the impact mitigating member may be disposed between the upper cap and the lower cap.

The first impact mitigating member may be curved to mitigate an impact transmitted to the cap from outside.

The first impact mitigating member may be eccentric to one side from a cross-sectional center of the cap.

The impact mitigating member may include an upper impact mitigating member protruding from the upper cap toward the lower cap and a lower impact mitigating member protruding from the lower cap toward the upper cap.

A thickness of the first impact mitigating member may be smaller than a thickness of the cap.

The impact mitigating member may further include a second impact mitigating member configured to cover the first impact mitigating member.

The second impact mitigating member may be formed as one body and disposed along a circumference of the cap.

A thickness of the second impact mitigating member may be larger than the thickness of the cap.

The second impact mitigating member may form the same plane as an inner side of the cap and may protrude further outward than an outer side of the cap.

The thickness of the second impact mitigating member may be equal to the thickness of the cap.

The impact mitigating member and the lower cap may be integrally formed of the same material.

The impact mitigating member may be disposed at a position that the ultrasound signal generated from the transducer does not reach in order to prevent transmission of the ultrasound signal generated from the transducer from being interfered with by the impact mitigating member.

In accordance with another aspect of the present disclosure, an ultrasonic probe includes a transducer configured to be movable, a cap including an operating portion configured to come in contact with an external subject and transmit an ultrasound signal generated by the transducer to the external subject and a cover portion extending from a lower portion of the operating portion, and an impact mitigating member disposed along a circumference of the cap to protect the cap from an external impact, wherein the impact mitigating member is disposed in the cover portion to prevent transmission of the ultrasound signal generated from the transducer from being interfered with by the impact mitigating member.

The impact mitigating member may include a first impact mitigating member having elasticity to mitigate an impact transmitted to the cap from outside.

The impact mitigating member may further include a second impact mitigating member configured to cover the first impact mitigating member to mitigate an impact transmitted to the cap from outside.

In accordance with still another aspect of the present disclosure, an ultrasonic probe includes a transducer configured to be movable, a cap including an upper cap configured to transmit the ultrasound signal generated by the transducer to outside and a lower cap disposed below the upper cap, and an impact mitigating member disposed between the upper cap and the lower cap to protect the cap from an external impact.

The impact mitigating member may include a first impact mitigating member extending from the cap to connect the upper cap to the lower cap and a second impact mitigating member configured to cover the first impact mitigating member.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
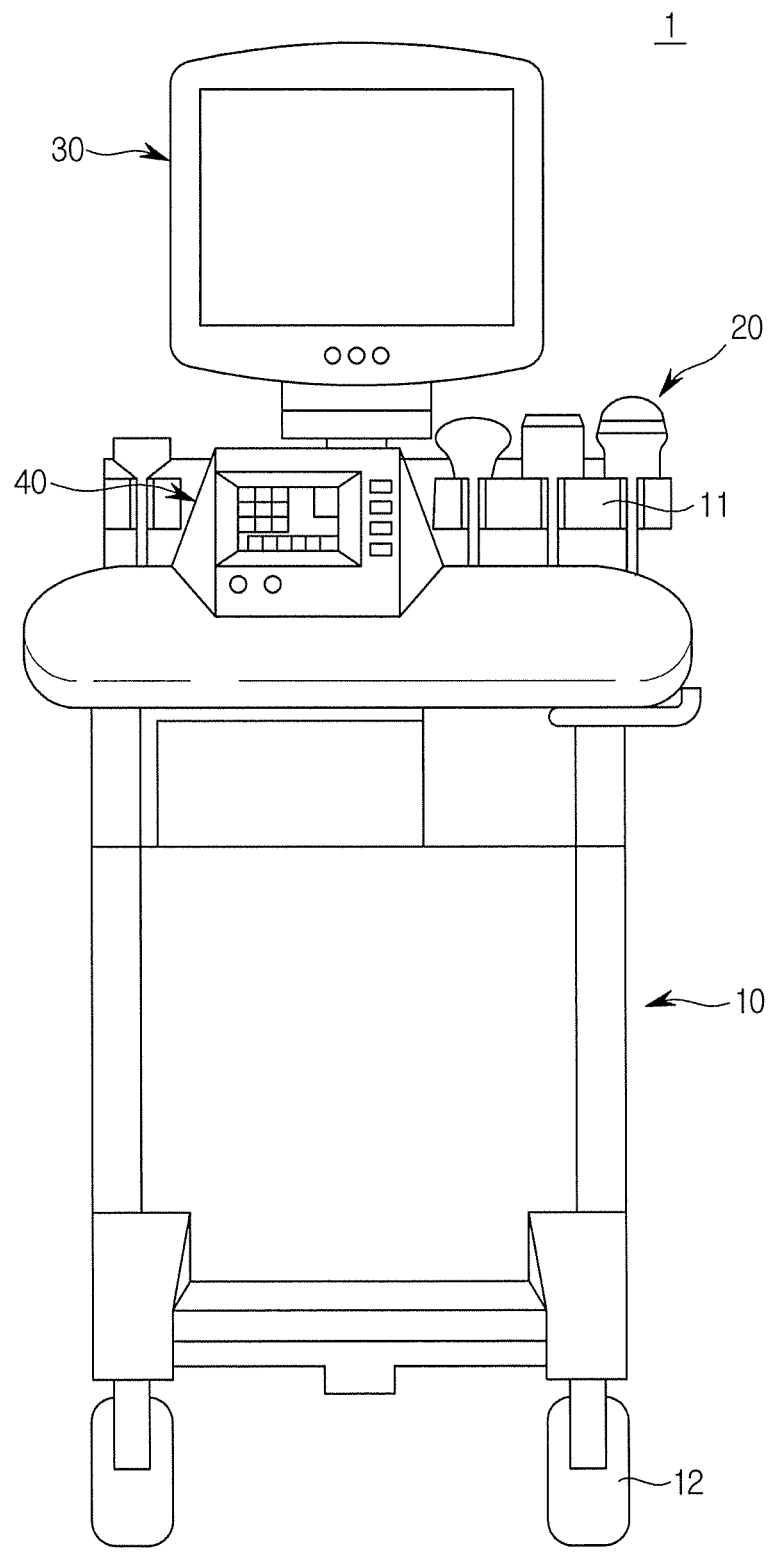
FIG. 1 is a view illustrating an ultrasound imaging device including an ultrasonic probe according to the present disclosure.

Various embodiments described herein and configurations illustrated in the drawings are merely exemplary embodiments of the present disclosure, and various modifications which may replace the embodiments and the drawings herein may be present at the time of filing this application.

Like reference numerals or symbols presented in the drawings of the application indicate parts or elements that perform substantially the same functions.

Terms used herein are for describing the embodiments and are not intended to limit and/or restrict the disclosure. A singular expression includes a plural expression unless context clearly indicates otherwise.

In the application, terms such as "include" or "have" should be understood as designating that features, number, steps, operations, elements, parts, or combinations thereof exist and not as precluding the existence of or the possibility of adding one or more other features, numbers, steps, operations, elements, parts, or combinations thereof in advance.

Terms including ordinals such as "first" and "second" may be used to describe various elements, but the elements are not limited by the terms. The terms are only used for the purpose of distinguishing one element from another element.

For example, a first element may be referred to as a second element while not departing from the scope of the present disclosure, and likewise, a second element may also be referred to as a first element. The term "and/or" includes a combination of a plurality of related described items or any one item among the plurality of related described items.

Terms such as "front," "rear," "upper portion," and "lower portion," when used in the description below, are defined on the basis of the drawings, and a shape and a position of each of the elements are not limited by the terms.

Hereinafter, exemplary embodiments of the present disclosure will be described in detail with reference to the accompanying drawings.

FIG. 1 is a view illustrating an ultrasound imaging device including an ultrasonic probe according to the present disclosure. Referring to FIG. 1, an ultrasound imaging device 1 according to the present disclosure may include a main body 10 and an ultrasonic probe 20 configured to transmit an ultrasound signal to a subject to be diagnosed and receive a signal reflected from the subject.

The ultrasonic probe 20 may be connected to the main body 10 via a cable. The main body 10 may include a display 30 configured to display a diagnosis result obtained through a received ultrasound signal. An application related to an operation of the ultrasound imaging device 1 may be displayed on the display 30.

As an example, an ultrasound image obtained in an ultrasound diagnosis process or details related to an operation of the ultrasound imaging device 1 may be displayed on the display 30.

The display 30 may be implemented with a cathode ray tube (CRT), a liquid crystal display (LCD) or the like. A plurality of displays 30 may be provided. When the plurality of displays 30 are provided, the displays 30 may include a main display and a sub-display.

As an example, an ultrasound image obtained in an ultrasound diagnosis process may be displayed on the main display, and details related to an operation of the ultrasound imaging device 1 may be displayed on the sub-display.

An input unit 40 may be disposed in the main body 10. The input unit 40 may be provided in the form of a keyboard, a foot switch, a foot pedal, or the like. When the input unit 40 is a keyboard, the input unit 40 may be disposed at an upper portion of the main body 10.

When the input unit 40 is a foot switch or a foot pedal, the input unit 40 may be disposed at a lower portion of the main body 10. An inspector may control an operation of the ultrasound imaging device 1 through the input unit 40.

The ultrasonic probe 20 may be mounted at the main body 10 using a holder 11. The inspector may mount the ultrasonic probe 20 in the holder 11 to store the ultrasonic probe 20 when not using the ultrasound imaging device 1.

A moving device 12 may be disposed in the main body 10 to move the ultrasound imaging device 1. The moving device 12 may be a plurality of castors disposed at a bottom surface of the main body 10.

The plurality of castors may be aligned to move the main body 10 in a specific direction, freely movable to move the main body 10 in any direction, or locked so that the main body 10 is stopped at a specific position.

Figure 2:
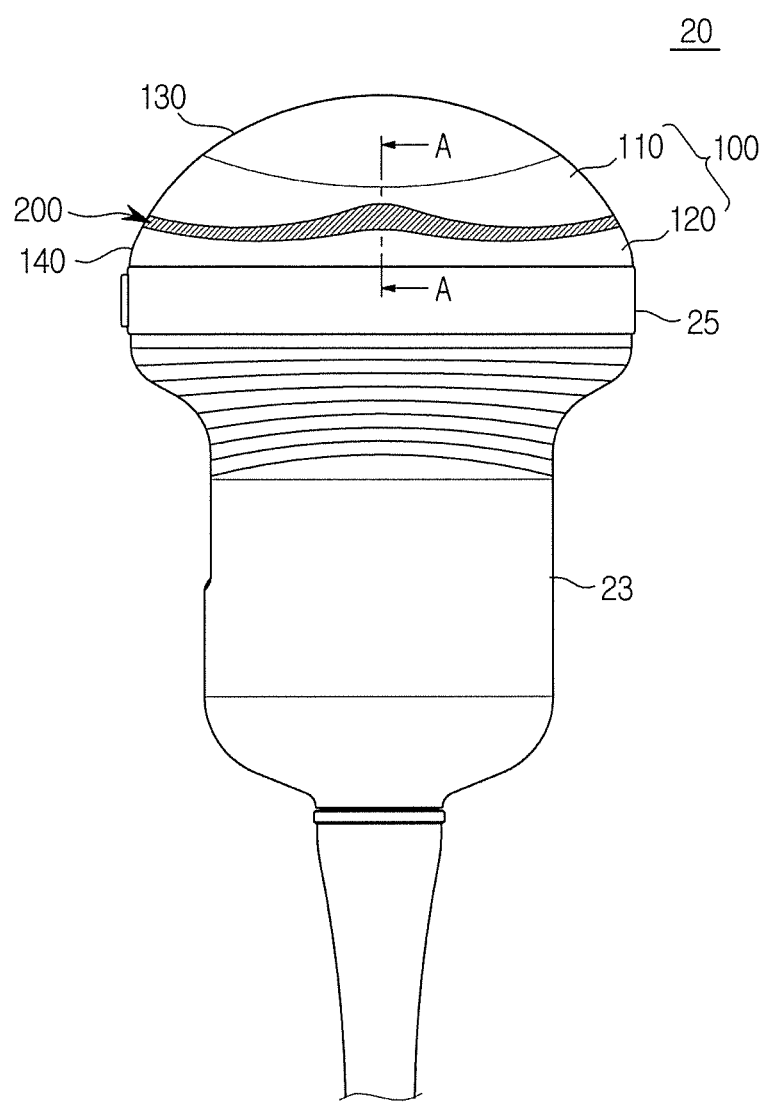
FIG. 2 is a view illustrating the ultrasonic probe according to one embodiment of the present disclosure.
Figure 3:
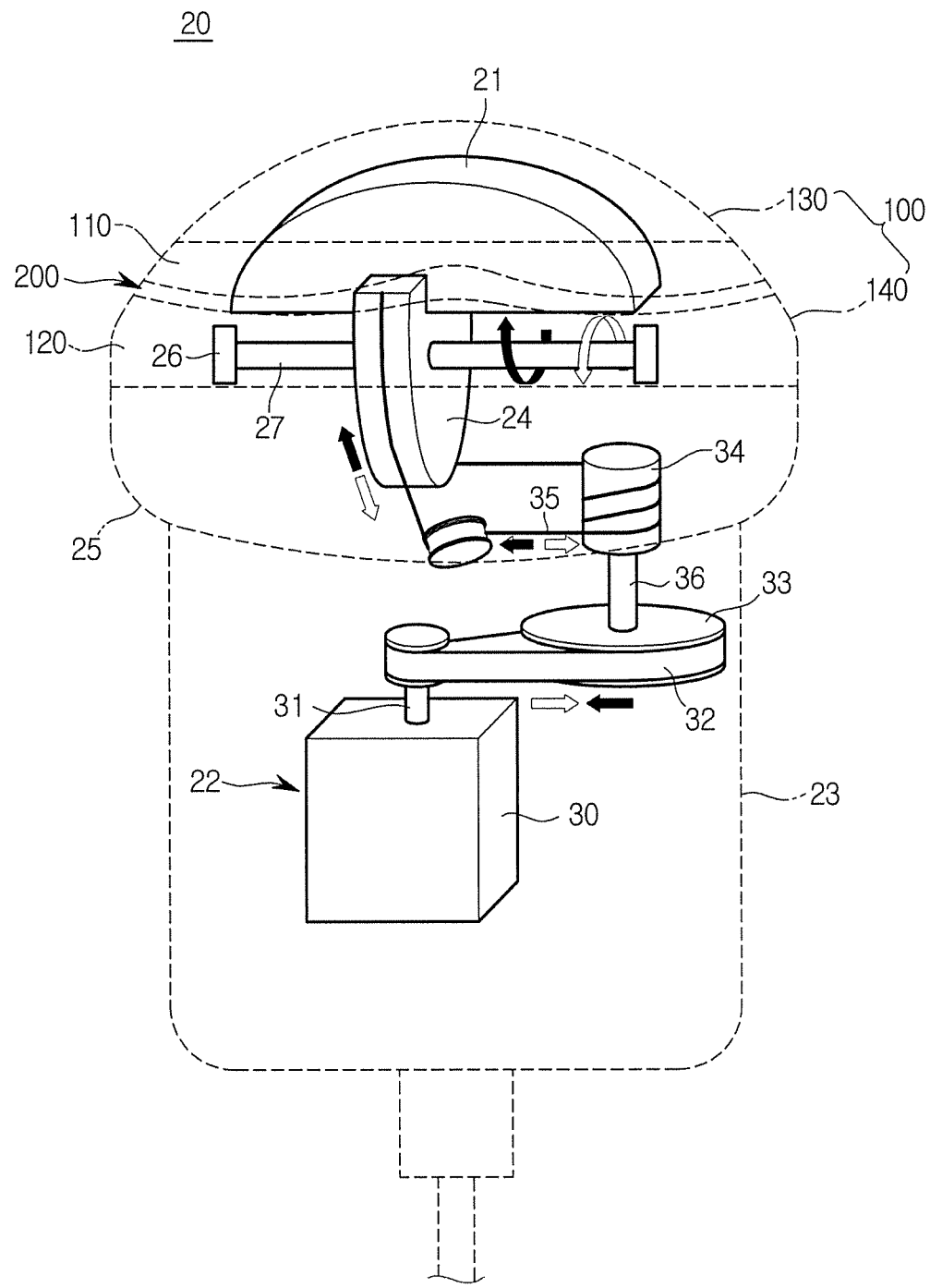
FIG. 3 is a view briefly illustrating an inner side of the ultrasonic probe according to one embodiment of the present disclosure.

FIG. 2 is a view illustrating the ultrasonic probe according to one embodiment of the present disclosure, and FIG. 3 is a view briefly illustrating an inner side of the ultrasonic probe according to one embodiment of the present disclosure.

Referring to FIGS. 2 and 3, the ultrasonic probe 20 according to one embodiment of the present disclosure may include a handle case 23 configured to be grasped by a user when using the ultrasonic probe 20.

The ultrasonic probe 20 may include a cap 100 disposed at a front end of the handle case 23 to come in contact with a subject to be diagnosed.

The cap 100 may be a convex type formed to have a convex central portion or a linear type having a flat surface. However, embodiments are not limited thereto.

Hereinafter, the ultrasonic probe 20 according to one embodiment of the present disclosure will be described on the basis of a convex type ultrasonic probe.

The ultrasonic probe 20 may include a base frame 25 disposed between the cap 100 and the handle case 23 to partition an inner space of the cap 100 and an inner space of the handle case 23.

The ultrasonic probe 20 may include a transducer 21 configured to be movable in the inner space of the cap 100.

The cap 100 may include an upper cap 110 configured to transmit an ultrasound signal generated by the transducer 21 to outside and a lower cap 120 disposed below the upper cap 110.

The ultrasonic probe 20 may include an impact mitigating member 200 to protect the cap 100 from an external impact. The impact mitigating member 200 may be disposed along a circumference of the cap 100. The impact mitigating member 200 may be disposed between the upper cap 110 and the lower cap 120.

Here, the circumference refers to an edge or boundary of the cap 100, and the circumference may include a portion of or an entire edge of the cap 100.

That is, the impact mitigating member 200 according to the present disclosure may be disposed along at least a portion of the circumference of the cap. The impact mitigating member 200 may also be disposed along an entire circumference of the cap 100.

A plurality of impact mitigating members 200 may be spaced apart and disposed along the circumference of the cap 100. The impact mitigating members 200 may be integrally connected and disposed along the circumference of the cap 100.

The impact mitigating member 200 may be formed as one body. However, embodiments are not limited thereto, and a plurality of impact mitigating members 200 may be disposed to be spaced apart from each other.

When the ultrasonic probe 20 does not include the impact mitigating member 200, the cap 100 itself may be damaged or a collision may occur between the cap 100 and the transducer 21 due to an external impact when an impact is applied to the cap 100 during use of the ultrasonic probe 20 due to a user's mistake.

When the cap 100 itself is damaged, the ultrasonic probe 20 may lose its own function. When the transducer 21 is damaged by a collision between the cap 100 and the transducer 21, an ultrasound image acquired by the transducer 21 may be significantly changed in comparison to that before an impact is applied to the transducer 21.

Consequently, after an impact is applied to the ultrasonic probe 20, reliability of an ultrasound image acquired by the transducer 21 may be degraded. Also, internal components of the ultrasonic probe 20 other than the transducer 21 may be damaged.

However, because the ultrasonic probe 20 according to the present disclosure includes the impact mitigating member 200 in the cap 100, an impact is mitigated by the impact mitigating member 200 even when an external impact is applied to the ultrasonic probe 20. Therefore, degradation of reliability on an ultrasound image or damage to the internal components may be prevented.

Generally, an ultrasonic probe includes an impact mitigating member that is formed as a protrusion at a front edge of a cap, and an impact transmitted to a transducer may be minimized by the impact mitigating member absorbing an impact first when an external impact is applied to the cap.

However, although the impact mitigating member formed as a protrusion at a front edge of a cap may be applied to a linear type cap, it may be structurally difficult for such an impact mitigating member to be applied to a convex type cap, which is actually used more commonly.

Because the impact mitigating member 200 is disposed at a circumferential portion of the cap 100 between the upper cap 110 and the lower cap 120 instead of being disposed at a front edge of the cap 100 in the ultrasonic probe 20 according to one embodiment of the present disclosure, the impact mitigating member 200 may be applied to a convex type cap as well as a linear type cap.

A specific structure of the above-described impact mitigating member 200 will be described below.

The transducer 21 may include an ultrasound transducer (not illustrated) configured to transmit and receive ultrasonic waves. The transducer 21 may be installed to be rotatable inside the cap 100 and read a three-dimensional image of a subject to be diagnosed.

The transducer 21 may be mounted at a shaft 27. The shaft 27 may receive a driving force from a driving device 22 and rotate. When the shaft 27 rotates, the transducer 21 mounted at the shaft 27 may also rotate.

The cap 100 may have an inner surface corresponding to an outer surface of the transducer 21 so that a predetermined distance between the inner surface of the cap 100 and the outer surface of the transducer 21 may be maintained even when the transducer 21 installed in the cap 100 rotates.

As an example, the outer surface of the transducer 21 and the inner surface of the cap 100 may be formed in arc shapes having the same center. However, embodiments are not limited thereto.

The inner space of the cap 100 may be filled with oil that serves as a medium to allow transmission of ultrasonic waves generated by the transducer 21. A pace formed by the cap 100 and the base frame 25 may be filled with oil.

The shaft 27 may receive a driving force from the driving device 22 and rotate. The driving device 22 may be accommodated inside the handle case 23. The driving device 22 may include a driving motor 30 and pulleys 31, 33, and 34 configured to receive a driving force from the driving motor 30. The driving device 22 may include wires 32 and 35 configured to transmit the driving force of the driving motor 30.

A first pulley 31 may receive the driving force of the driving motor 30 and rotate. A first wire 32 may connect the first pulley 31 to a second pulley 33. The driving force transmitted to the first pulley 31 may be transmitted to the second pulley 33 by the first wire 32.

The second pulley 33 and a third pulley 34 may be connected by a second transmitting member. As an example, the second transmitting member 36 may be a shaft configured to connect the second pulley 33 and the third pulley 34.

The second pulley 33 and the third pulley 34 may be respectively fixed to one end and the other end of the second transmitting member 36, which is the shaft. In this way, when the second pulley 33 receives the driving force and rotates, the third pulley 34 may also rotate.

However, the type of the second transmitting member 36 is not limited to a shaft. The second transmitting member 36 may be properly configured according to a configuration of a space in the handle case 23. The second transmitting member 36 may be a configuration including a pulley and a wire or a configuration formed by connecting gears.

A first transmitting member 24 may be mounted at the shaft 27. The first transmitting member 24 may be fixed to one side of the shaft 27 and rotate together with the shaft 27. The first transmitting member 24 and the third pulley 34 may be connected by a second wire 35.

When the third pulley 34 rotates, a rotary force may be transmitted to the first transmitting member 24 by the second wire 35, and the first transmitting member 24 may rotate. Here, the shaft 27 may rotate together with the first transmitting member 24.

The second wire 35 may be wound around the third pulley 34 and configured to cover a portion of an outer circumferential surface of the first transmitting member 24.

The shaft 27 may be rotatably mounted at a support member 26. The support member 26 may protrude from the base frame 25. The shaft 27 may be mounted at the support member 26, receive a driving force from the driving device 22, and rotate in one direction or the other direction.

The support member 26 may be formed of a metal material that is rigid to support the shaft 27 and is capable of flexibly withstanding an external impact. As an example, the support member 26 may be formed of a metal material including aluminum. However, embodiments are not limited thereto.

An insertion hole (not illustrated) into which the shaft 27 is inserted may be formed in the support member 26. The shaft 27 may be inserted into the insertion hole (not illustrated) and fixed. A diameter of the insertion hole (not illustrated) may be somewhat larger than or equal to that of the shaft 27.

The cap 100 may include an operating portion 130 configured to come in contact with an external subject and transmit an ultrasound signal generated by the transducer 21 to the external subject and a cover portion 140 extending from a lower portion of the operating portion 130.

Because the transducer 21 rotates at a predetermined angle in conjunction with rotations of the shaft 27 and the first transmitting member 24, the cap 100 may include the operating portion 130 through which an ultrasound signal generated from the transducer 21 passes and the cover portion 140 through which the ultrasound signal generated from the transducer 21 does not pass.

The operating portion 130 may include a substantially arc-shaped cross-section according to the range of rotation of the transducer 21. However, embodiments are not limited thereto.

The impact mitigating member 200 may be disposed in the cover portion 140, instead of being disposed in the operating portion 130, to prevent transmission of an ultrasound signal generated from the transducer 21 from being interfered with by the impact mitigating member 200.

The upper cap 110 may include the operating portion 130. The cover 140 may include the lower cap 120.

That is, the impact mitigating member 200 may be disposed at a position that the ultrasound signal generated from the transducer 21 does not reach in order to prevent transmission of the ultrasound signal generated from the transducer 21 from being interfered with by the impact mitigating member 200.

The impact mitigating member 200 may be disposed at various positions in the cover portion 140 off the cap 100 within the range of positions that an ultrasound signal does not reach.

The operating portion 130 may come into contact with an external subject and directly receive an external impact. The impact mitigating member 200 may be disposed at one end of the operating portion 130 to mitigate an external impact received by the operating portion 130. The impact mitigating member 200 may be disposed at a lower portion of the operating portion 130.

That is, the impact mitigating member 200 may indirectly mitigate an impact that the operating portion 130 receives from the outside.

Generally, an impact mitigating member is provided in the shape of a protrusion at a front edge of a cap to mitigate an impact acted on the cap from the outside. When a user drops an ultrasonic probe by mistake while using the ultrasonic probe, the impact mitigating member, instead of an operating portion, may directly collide with the ground to prevent an impact from being directly transmitted to the operating portion.

That is, the impact mitigating member in the shape of a protrusion may directly mitigate an external impact that the operating portion receives. Although, as described, the impact mitigating member in the shape of a protrusion may be applied to a linear type cap, there may be difficulty in applying the impact mitigating member in the shape of a protrusion to a convex type cap.

Unlike this, the impact mitigating member 200 according to the present disclosure is disposed at a lower portion of the operating portion 130, and although the operating portion 130 may directly collide with the ground when the user drops the ultrasonic probe 20 by mistake while using the ultrasonic probe 20, the impact mitigating member 200 may indirectly mitigate an external impact acted on the operating portion 130.

Consequently, the ultrasonic probe 20 according to the present disclosure may come into contact with an external subject through the operating portion 130 without being interfered with by the impact mitigating member 200 and efficiently perform an essential function of the ultrasonic probe 20, and may also mitigate an external impact acted on the operating portion 130 by the impact mitigating member 200.

Particularly, the impact mitigating member 200 according to the present disclosure may be applied to a convex type cap, to which the impact mitigating member in the shape of a protrusion protruding from the front edge of the cap 100 is difficult to be applied, without limitation.

Figure 4:
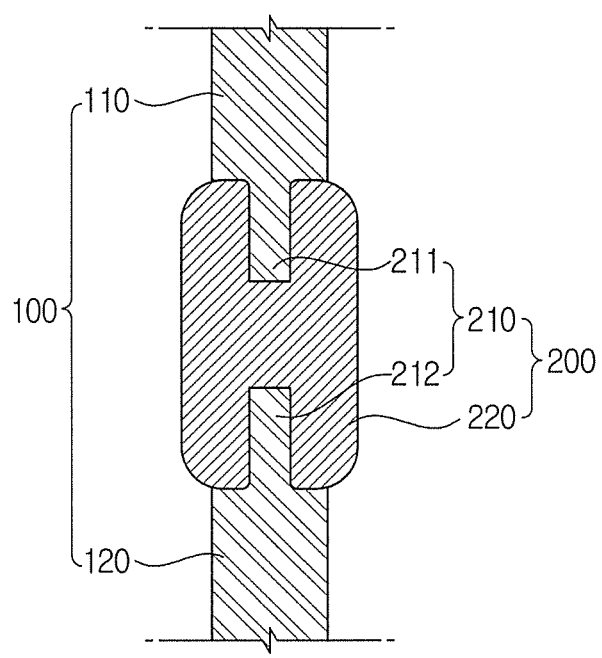
FIG. 4 is a cross-sectional view taken along line A-A of FIG. 2 of a cap and an impact mitigating member of the ultrasonic probe according to one embodiment of the present disclosure illustrated in FIG. 2.
Figure 5:
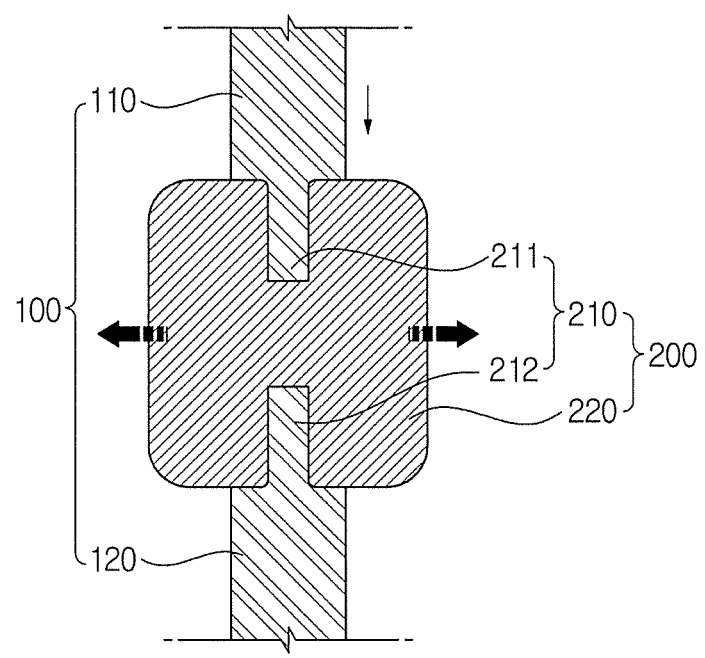
FIG. 5 is a view illustrating a state in which an impact is applied from outside to the cap of the ultrasonic probe according to one embodiment of the present disclosure illustrated in FIG. 4.

FIG. 4 is a cross-sectional view taken along line A-A of FIG. 2 of a cap and an impact mitigating member of the ultrasonic probe according to one embodiment of the present disclosure illustrated in FIG. 2. FIG. 5 is a view illustrating a state in which an impact is applied from outside to the cap of the ultrasonic probe according to one embodiment of the present disclosure illustrated in FIG. 4

As illustrated in FIGS. 4 and 5, the ultrasonic probe 20 may include the cap 100 configured to protect the ultrasonic probe 20 and the impact mitigating member 200 disposed between the upper cap 110 and the lower cap 120.

The impact mitigating member 200 may include a first impact mitigating member 210 extending from the cap 100 to connect the upper cap 110 and the lower cap 120.

The first impact mitigating member 210 may include an upper impact mitigating member 211 protruding from the upper cap 110 toward the lower cap 120 and a lower impact mitigating member 212 protruding from the lower cap 120 toward the upper cap 110. The impact mitigating member 200 may include a second impact mitigating member 220 configured to cover the first impact mitigating member 210.

The second impact mitigating member 220 may be formed by being double injection-molded with the first impact mitigating member 210 and the cap 100. However, embodiments are not limited thereto.

The impact mitigating member 200 may have elasticity to be deformed by an external impact and be returned to its original state when the external impact is removed.

When an impact is applied to the ultrasonic probe 20 and an impact is generated between the cap 100 and the transducer 21, such as when the ultrasonic probe 20 is dropped due to carelessness of a user during use of the ultrasonic probe 20, a force applied to the cap 100 may be mitigated by the impact mitigating member 200.

That is, when an external force acts on the upper cap 110 in a direction toward the lower cap 120, the impact mitigating member 200 may be deformed in a direction perpendicular to the above direction and offset the external force.

A thickness of the first impact mitigating member 210 may be smaller than a thickness of the cap 100. That is, the first impact mitigating member 210 may, due to its structural aspects, primarily mitigate an impact applied to the cap 100.

A thickness of the second impact mitigating member 220 may be larger than the thickness of the cap 100. That is, the second impact mitigating member 220 may protrude further than one side surface of the cap 100. However, embodiments are not limited thereto.

The second impact mitigating member 220 may be formed of a material capable of absorbing an impact. As an example, the second impact mitigating member 220 may be formed of an elastic material such as an elastomer and plastic.

Consequently, after the impact applied to the cap 100 is primarily mitigated by the first impact mitigating member 210, the second impact mitigating member 220 may, due to its material, mitigate the impact applied to the cap 100 further.

The first impact mitigating member 210 may have various forms and serve to mitigate an impact applied to the cap 100. Hereinafter, various embodiments of the first impact mitigating member 210 and the second impact mitigating member 220 will be described in detail.

FIGS. 6 to 14 are cross-sectional views taken along line A-A of FIG. 2 of a cap and an impact mitigating member of an ultrasonic probe according to other embodiments of the present disclosure.

As illustrated in FIGS. 6 to 14, the ultrasonic probe 20 may include the cap 100 configured to protect the ultrasonic probe 20 and the impact mitigating member 200 disposed between the upper cap 110 and the lower cap 120.

Figure 6:
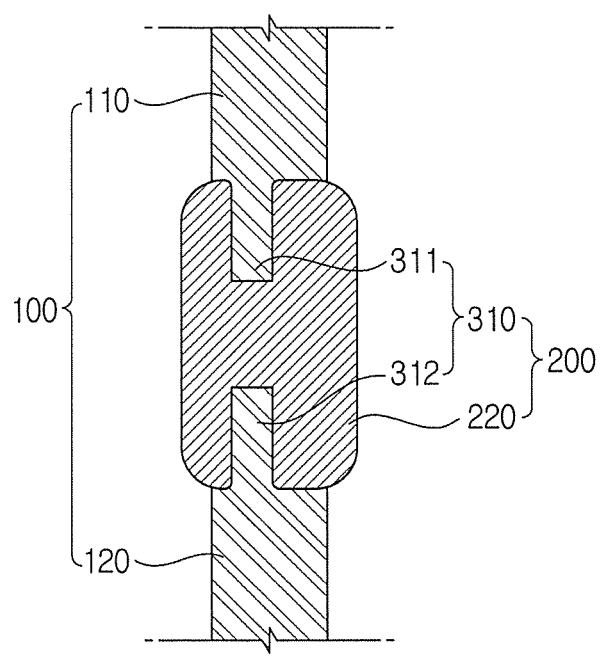
FIGS. 6 to 14 are cross-sectional views taken along line A-A of FIG. 2 of a cap and an impact mitigating member of an ultrasonic probe according to other embodiments of the present disclosure.

Referring to FIG. 6, a first impact mitigating member 310 may be eccentric to one side from a cross-sectional center of the cap 100. That is, an upper impact mitigating member 311 and a lower impact mitigating member 312 may be disposed to be eccentric to one side of the cap 100.

The first impact mitigating member 310 may be disposed to be eccentric further toward an inside of the cap 100 than an outside thereof. However, embodiments are not limited thereto.

The second impact mitigating member 220 may be disposed between the upper cap 110 and the lower cap 120 to cover the first impact mitigating member 310.

Figure 7:
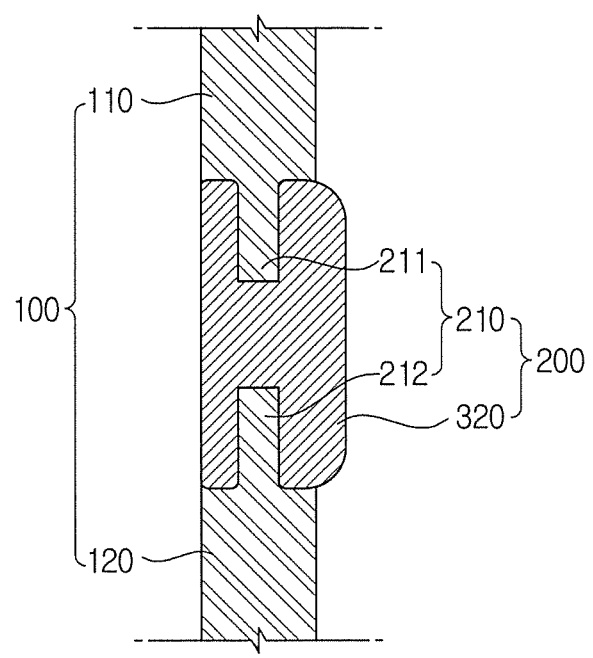

Referring to FIG. 7, the second impact mitigating member 320 may form the same plane as one side of the cap 100 and may protrude further outward than the other side of the cap 100. The second impact mitigating member 320 may form the same plane as an inner side of the cap 100 and may protrude further outward than an outer side of the cap 100.

Because a space configured to accommodate internal components such as the transducer 21 (see FIG. 3) is required inside the cap 100, the second impact mitigating member 320 may form the same plane as the inner side of the cap 100. However, embodiments are not limited thereto.

The second impact mitigating member 320 may be disposed between the upper cap 110 and the lower cap 120 to cover the first impact mitigating member 210.

Figure 8:
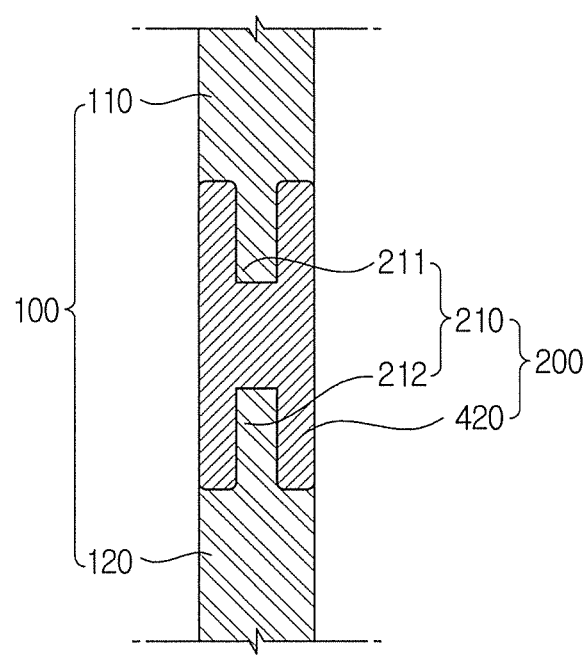

Referring to FIG. 8, a thickness of a second impact mitigating member 420 may be equal to the thickness of the cap 100. That is, the second impact mitigating member 420 may form the same plane as the inner side and the outer side of the cap 100.

Because a space configured to accommodate internal components such as the transducer 21 (see FIG. 3) is required inside the cap 100, the second impact mitigating member 420 may form the same plane as the inner side of the cap 100.

The second impact mitigating member 420 may also form the same plane as the outer side of the cap 100 to improve the design of an exterior of the cap and reduce an overall volume of the ultrasonic probe 20.

The second impact mitigating member 420 may be disposed between the upper cap 110 and the lower cap 120 to cover the first impact mitigating member 210.

Figure 9:
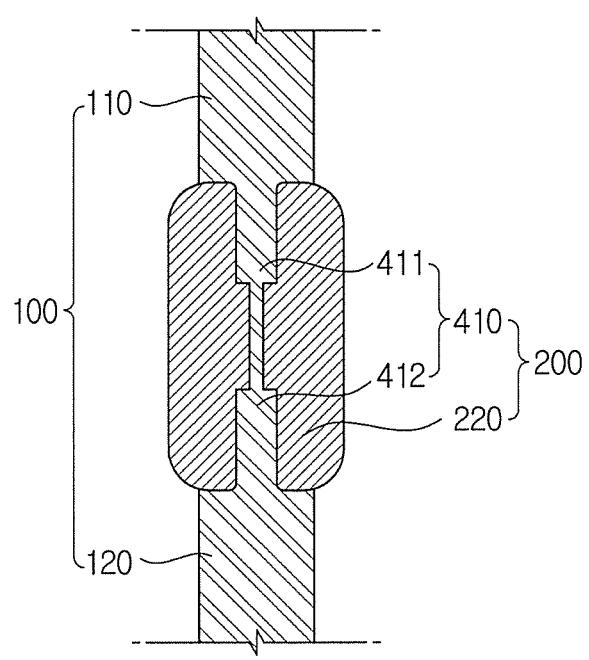

Referring to FIG. 9, an upper impact mitigating member 411 and a lower impact mitigating member 412 may be integrally formed with each other. That is, the upper impact mitigating member 411 may extend toward the lower impact mitigating member 412, and the lower impact mitigating member 412 may extend toward the upper impact mitigating member 411. In this way, a first impact mitigating member 410 may be formed as one body.

A thickness of a portion extending from the upper impact mitigating member 411 and the lower impact mitigating member 412 may be smaller than thicknesses of the upper impact mitigating member 411 and the lower impact mitigating member 412. That is, the first impact mitigating member 410 may include a thin partition structure. However, embodiments are not limited thereto.

The second impact mitigating member 220 may be disposed between the upper cap 110 and the lower cap 120 to cover the first impact mitigating member 410.

Figure 10:
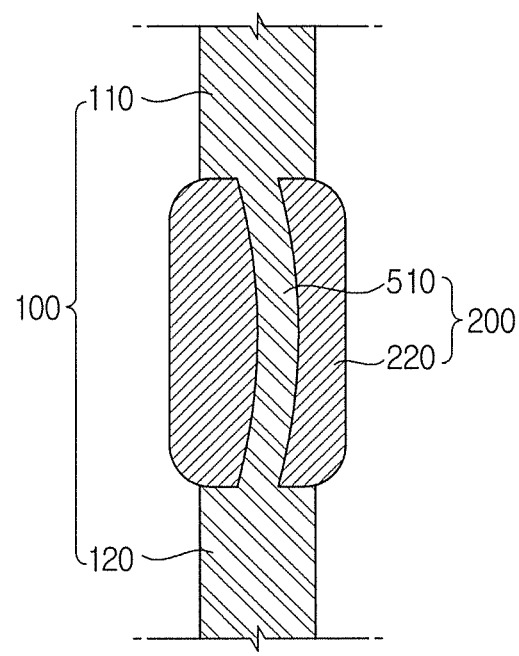

Referring to FIG. 10, a first impact mitigating member 510 may be formed as one body. The first impact mitigating member 510 may be curved toward one side of the cap 100 to mitigate an impact transmitted to the cap 100 from outside.

The first impact mitigating member 510 may be curved toward the outer side of the cap 100. However, embodiments are not limited thereto. The first impact mitigating member 510 may have a curvature.

The first impact mitigating member 510 may connect the upper cap 110 and the lower cap 120 to have a curved surface. That is, the first impact mitigating member 510 may be longer than the shortest possible distance between the upper cap 110 and the lower cap 120.

The second impact mitigating member 220 may be disposed between the upper cap 110 and the lower cap 120 to cover the first impact mitigating member 510.

Figure 11:
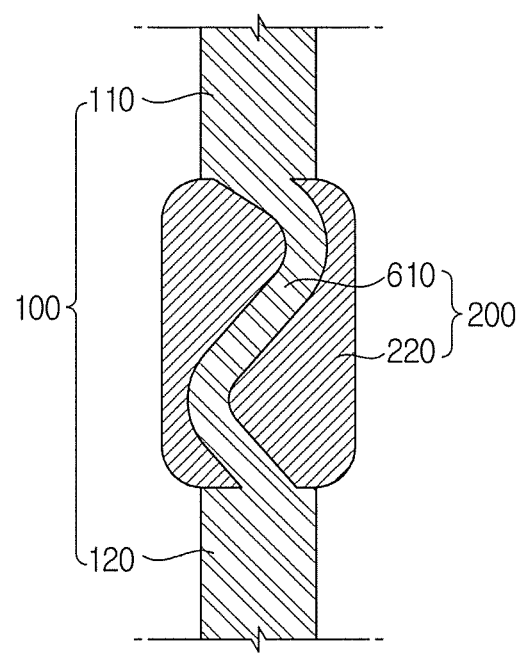

Referring to FIG. 11, a first impact mitigating member 610 may be formed as one body. The first impact mitigating member 610 may be curved toward both sides of the cap 100 to mitigate an impact transmitted to the cap 100 from outside. The first impact mitigating member 610 may be formed in a substantially S-shape. However, embodiments are not limited thereto.

The first impact mitigating member 610 may connect the upper cap 110 and the lower cap 120 to have a curved surface. That is, the first impact mitigating member 610 may be longer than the shortest possible distance between the upper cap 110 and the lower cap 120.

Starting from the upper cap 110, the first impact mitigating member 610 may deviate toward the outer side and the inner side of the cap 100 two times or more and be connected to the lower cap 120.

The second impact mitigating member 220 may be disposed between the upper cap 110 and the lower cap 120 to cover the first impact mitigating member 610.

Figure 12:
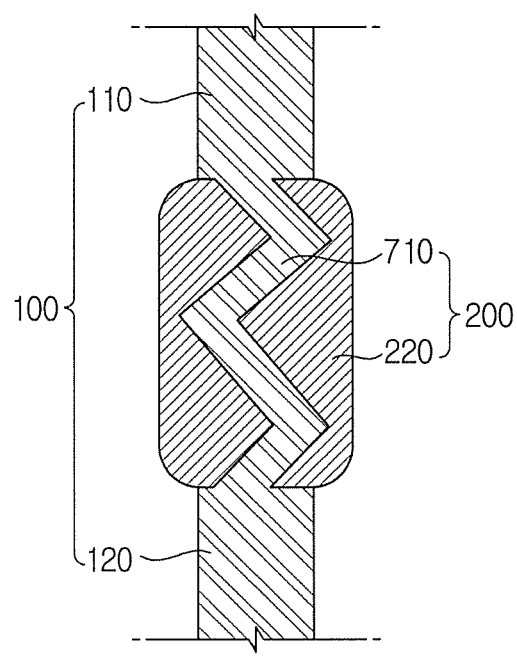

Referring to FIG. 12, a first impact mitigating member 710 may be formed as one body. The first impact mitigating member 710 may be inclined toward both sides of the cap 100 to mitigate an impact transmitted to the cap 100 from outside.

The first impact mitigating member 710 may be inclined in a zigzag shape and form a spring-like shape. However, embodiments are not limited thereto.

The first impact mitigating member 710 may connect the upper cap 110 and the lower cap 120 to form a slope. That is, the first impact mitigating member 710 may be longer than the shortest possible distance between the upper cap 110 and the lower cap 120.

Starting from the upper cap 110, the first impact mitigating member 710 may be bent toward the outer side and the inner side of the cap 100 two times or more and be connected to the lower cap 120.

The second impact mitigating member 220 may be disposed between the upper cap 110 and the lower cap 120 to cover the first impact mitigating member 710.

Figure 13:
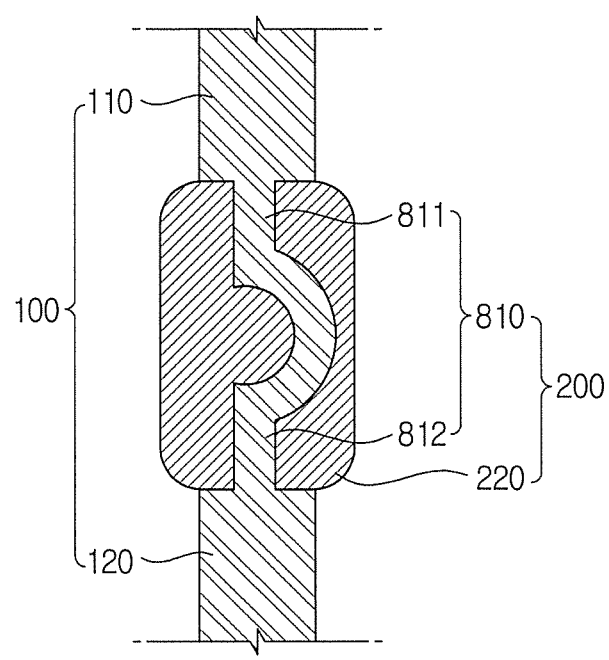

Referring to FIG. 13, a first impact mitigating member 810 may be formed as one body. Starting from an upper impact mitigating member 811, the first impact mitigating member 810 may deviate toward one side and be connected to a lower impact mitigating member 812.

The first impact mitigating member 810 may be curved toward one side of the cap 100 to mitigate an impact transmitted to the cap 100 from outside. The first impact mitigating member 810 may be curved toward the outer side of the cap 100. The first impact mitigating member 810 may include a substantially semicircular shape. However, embodiments are not limited thereto.

The first impact mitigating member 810 may connect the upper impact mitigating member 811 and the lower impact mitigating member 812 to form a curved surface. That is, the first impact mitigating member 810 may be longer than the shortest possible distance between the upper impact mitigating member 811 and the lower impact mitigating member 812.

The second impact mitigating member 220 may be disposed between the upper cap 110 and the lower cap 120 to cover the first impact mitigating member 810.

Figure 14:
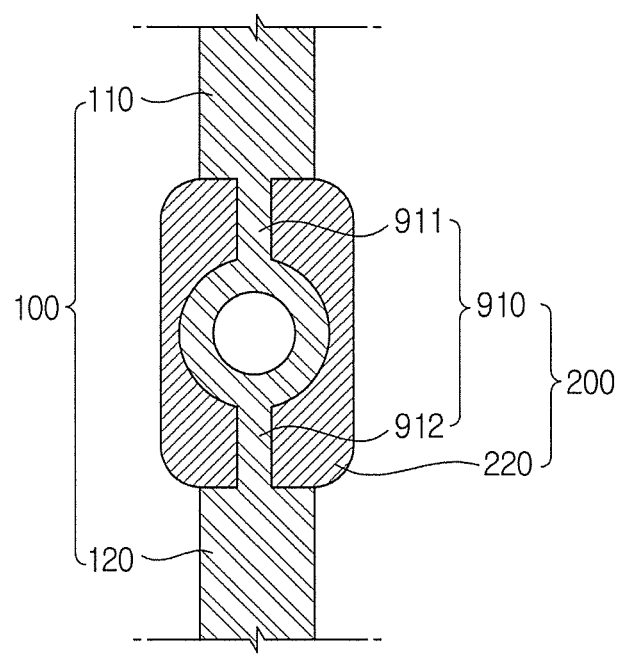

Referring to FIG. 14, a first impact mitigating member 910 may be formed a one body. The first impact mitigating member 910 may detour toward both sides of the cap 100 to connect an upper impact mitigating member 911 and a lower impact mitigating member 912 and may have a hollow space therein.

The first impact mitigating member 910 may be curved toward both sides of the cap 100 to mitigate an impact transmitted to the cap 100 from outside. The first impact mitigating member 910 may include a substantially circular shape. However, embodiments are not limited thereto.

The first impact mitigating member 910 may connect the upper impact mitigating member 911 and the lower impact mitigating member 912 to form a curved surface. That is, the first impact mitigating member 910 may be longer than the shortest possible distance between the upper impact mitigating member 911 and the lower impact mitigating member 912.

The second impact mitigating member 220 may be disposed between the upper cap 110 and the lower cap 120 to cover the first impact mitigating member 910.

However, the embodiments in which the first impact mitigating members 210, 310, 410, 510, 610, 710, 810, and 910 have elasticity due to their own shapes are not limited to the embodiments illustrated in FIGS. 6 to 14.

That is, the first impact mitigating members 210, 310, 410, 510, 610, 710, 810, and 910 may have various shapes and serve as the impact mitigating member 200 configured to mitigate an external impact.

Figure 15:
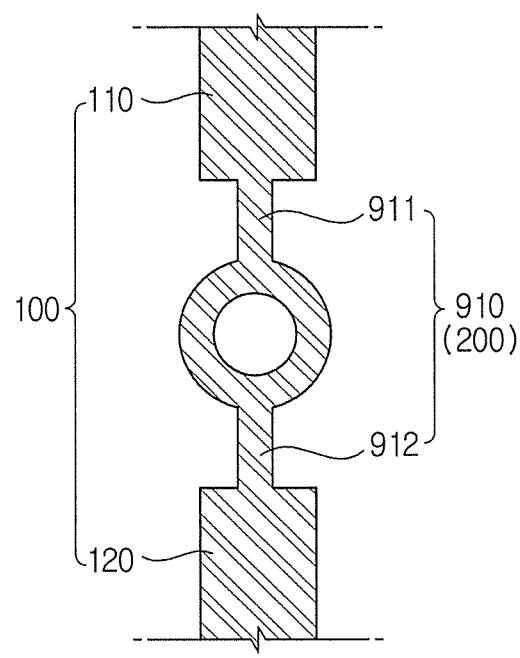
FIG. 15 is a cross-sectional view taken along line A-A of FIG. 2 of a cap and a first impact mitigating member of an ultrasonic probe according to still another embodiment of the present disclosure.

FIG. 15 is a cross-sectional view taken along line A-A of FIG. 2 of a cap and a first impact mitigating member of an ultrasonic probe according to still another embodiment of the present disclosure. As illustrated in FIG. 15, the impact mitigating member 200 may include only the first impact mitigating member 910.

That is, the impact mitigating member 200 may mitigate an impact from outside using only the structure of the first impact mitigating member 910 and without the second impact mitigating member 220 (see FIG. 4).

Consequently, because the ultrasonic probe 20 according to the embodiment illustrated in FIG. 15 does not include the second impact mitigating member 220 (see FIG. 4), a production cost of the ultrasonic probe 20 may be reduced.

Although the first impact mitigating member 910 is illustrated in FIG. 15 as having the same structure as that of the first impact mitigating member 910 illustrated in FIG. 14, embodiments are not limited thereto, and the first impact mitigating member 910 may include various shapes including all of the structure of the first impact mitigating members 410, 510, 610, 710, 810, and 910 illustrated in FIGS. 9 to 14.

By having a length longer than the shortest possible distance between the upper cap 110 and the lower cap 120 and deviating toward the inner side or the outer side of the cap 100 to connect the upper cap 110 and the lower cap 120 as described above, the first impact mitigating members 410, 510, 610, 710, 810, and 910 may have a predetermined amount of elasticity.

The first impact mitigating members 210, 310, 410, 510, 610, 710, 810, and 910 may be temporarily deformed by an external force but may be restored to its original shape when the external force is removed. Consequently, the first impact mitigating members 210, 310, 410, 510, 610, 710, 810, and 910 may elastically support the upper cap 110 and the lower cap 120.

Figure 16:
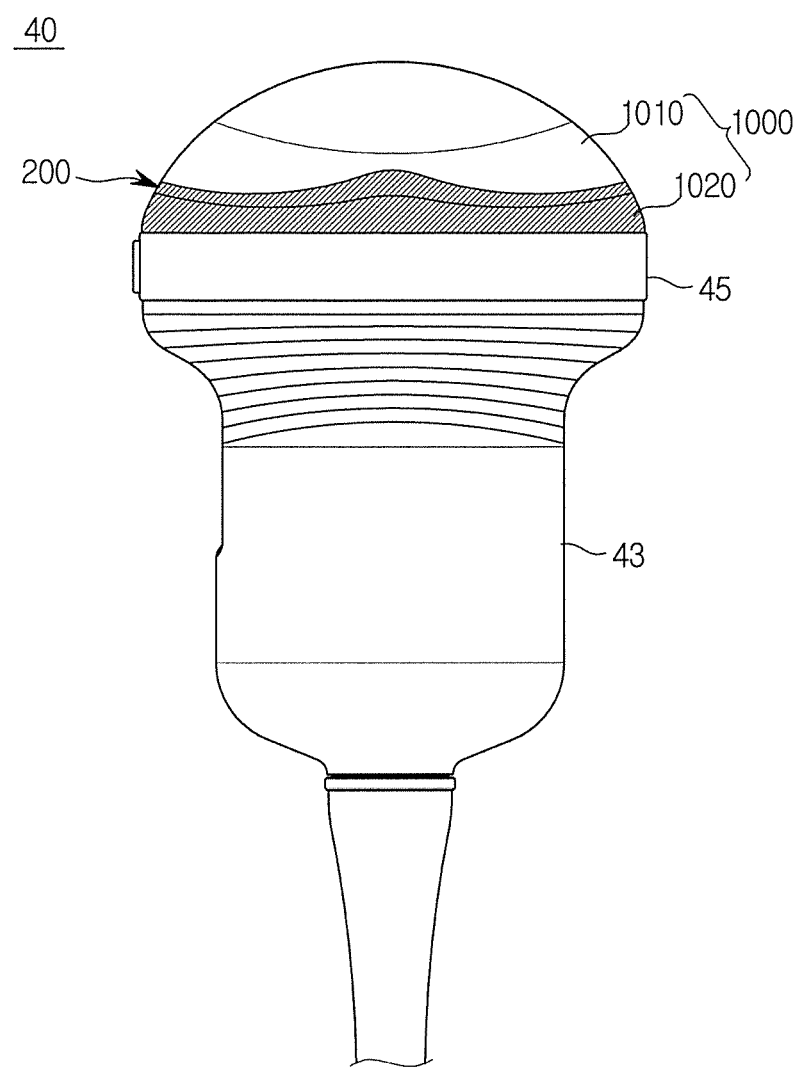
FIGS. 16 and 17 are views illustrating an ultrasonic probe according to yet other embodiments of the present disclosure.
Figure 17:
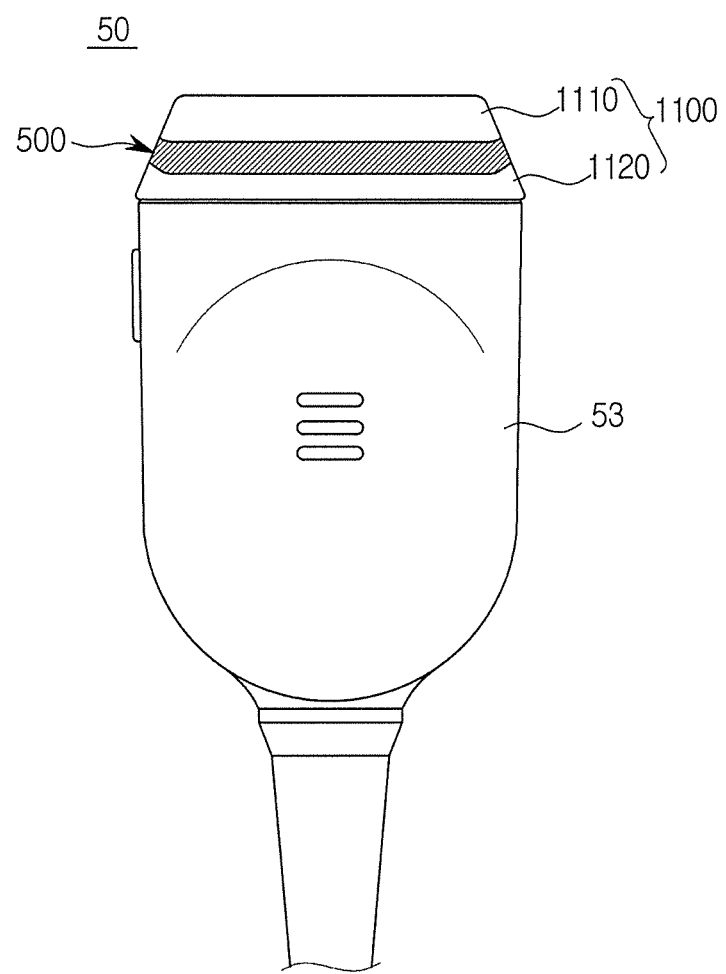

FIGS. 16 and 17 are views illustrating an ultrasonic probe according to yet other embodiments of the present disclosure. Configurations of ultrasonic probes 40 and 50 according to the yet other embodiments of the present disclosure illustrated in FIGS. 16 and 17 are mostly the same as that of the ultrasonic probe 20 according to one embodiment of the present disclosure.

Hereinafter, the ultrasonic probes 40 and 50 according to the yet other embodiments of the present disclosure will be described mainly on the basis of differences from the ultrasonic probe 20 according to one embodiment of the present disclosure.

As illustrated in FIG. 16, the ultrasonic probe 40 according to yet another embodiment of the present disclosure may include a handle case 43 configured to be grasped by a user when using the ultrasonic probe 40.

The ultrasonic probe 40 may include a cap 1000 that may be disposed at a front end of the handle case 43 to come in contact with a subject to be diagnosed.

The cap 1000 may be a convex type formed to have a convex central portion or a linear type having a flat surface. However, embodiments are not limited thereto.

Hereinafter, the ultrasonic probe 40 according to yet another embodiment of the present disclosure will be described on the basis of a convex type ultrasonic probe.

The ultrasonic probe 40 may include a base frame 45 disposed between the cap 1000 and the handle case 43 to partition an inner space of the cap 1000 and an inner space of the handle case 43.

The cap 1000 may include an upper cap 1010 and a lower cap 1020 disposed below the upper cap 1010.

The ultrasonic probe 40 may include an impact mitigating member 200 disposed between the upper cap 1010 and the lower cap 1020 to protect the cap 1000 from an external impact.

The impact mitigating member 200 and the lower cap 1020 may be integrally formed with the same material. Because the lower cap 1020 may perform a function of mitigating an impact together with the impact mitigating member 200 in the ultrasonic probe 40 according to yet another embodiment of the present disclosure, a superior impact mitigation effect may be exhibited.

As illustrated in FIG. 17, the ultrasonic probe 50 according to yet another embodiment of the present disclosure may include a handle case 53 configured to be grasped by a user when using the ultrasonic probe 50.

The ultrasonic probe 50 may include a cap 1100 that may be disposed at a front end of the handle case 53 to come in contact with a subject to be diagnosed. The cap 1100 of the ultrasonic probe 50 according to yet another embodiment of the present disclosure may be a linear type having a flat surface.

The cap 1100 may include an upper cap 1110 and a lower cap 1120 disposed below the upper cap 1110. The ultrasonic probe 50 may include an impact mitigating member 500 disposed between the upper cap 1110 and the lower cap 1120 to protect the cap 1100 from an external impact.

Consequently, because the impact mitigating members 200 and 500 are disposed at circumferential portions of the caps 100 and 1100 between the upper caps 110 and 1110 and the lower caps 120 and 1120 instead of being disposed at front edges of the caps 100 and 1100 in the ultrasonic probes 20 and 50 according to the present disclosure, the impact mitigating members 200 and 500 may be applied to both the convex type cap 100 and the linear type cap 1100.

As is apparent from the above description, according to the present disclosure, a cap and internal components of the cap can, through the deformation of a circumferential structure of the cap, be prevented from being damaged by an external impact.

According to the present disclosure, an impact applied to the cap from outside can be mitigated and components disposed inside an ultrasonic probe can, by having an impact mitigating member disposed along a circumference of the cap, be prevented from being damaged.

Although the technical idea of the present disclosure according to specific embodiments have been described above, the scope of the present disclosure is not limited to the above embodiments.

Various embodiments that may be made by one of ordinary skill in the art to which the present disclosure pertains by modifying or changing the above embodiments within the scope not departing from the gist of the technical idea of the present disclosure defined by the appended claims also belong to the scope of the present disclosure.

What is claimed is:

1. An ultrasonic probe comprising:
    a transducer configured to be movable;
    a cap configured to transmit an ultrasound signal generated by the transducer to outside;
    a base frame connected to the cap so that an inner space of the cap is filled with oil; and
    an impact mitigating member disposed entirely on the cap to protect the cap from an external impact,
    wherein a portion of the cap extends between the impact mitigating member and the base frame.

2. The ultrasonic probe of claim 1, wherein the impact mitigating member is disposed along at least a portion of a circumference of the cap.

3. The ultrasonic probe of claim 1, wherein the impact mitigating member includes a first impact mitigating member having elasticity to be deformed by an external impact and be returned to its original state when the external impact is removed.

4. The ultrasonic probe of claim 1, wherein:
    the cap includes an upper cap configured to come in contact with an external subject and transmit the ultrasound signal generated by the transducer to the external subject and a lower cap disposed below the upper cap; and
    the impact mitigating member is disposed between the upper cap and the lower cap.

5. The ultrasonic probe of claim 3, wherein the first impact mitigating member is curved to mitigate an impact transmitted to the cap from outside.

6. The ultrasonic probe of claim 3, wherein the first impact mitigating member is eccentric to one side from a cross-sectional center of the cap.

7. The ultrasonic probe of claim 4, wherein the impact mitigating member includes: an upper impact mitigating member protruding from the upper cap toward the lower cap; and a lower impact mitigating member protruding from the lower cap toward the upper cap.

8. The ultrasonic probe of claim 3, wherein a thickness of the first impact mitigating member is smaller than a thickness of the cap.

9. The ultrasonic probe of claim 3, wherein the impact mitigating member further includes a second impact mitigating member having elasticity and configured to cover the first impact mitigating member.

10. The ultrasonic probe of claim 9, wherein the second impact mitigating member is disposed along an entire circumference of the cap.

11. The ultrasonic probe of claim 9, wherein a thickness of the second impact mitigating member is larger than the thickness of the cap.

12. The ultrasonic probe of claim 11, wherein the second impact mitigating member forms the same plane as an inner side of the cap and protrudes further outward than an outer side of the cap.

13. The ultrasonic probe of claim 9, wherein the thickness of the second impact mitigating member is equal to the thickness of the cap.

14. The ultrasonic probe of claim 4, wherein the impact mitigating member and the lower cap are integrally formed of the same material.

15. The ultrasonic probe of claim 1, wherein:
the cap includes an operating portion configured to come into contact with an external subject and directly receive an external impact; and
the impact mitigating member is disposed at a lower portion of the operating portion to mitigate an external impact that the operating portion receives.

16. An ultrasonic probe comprising:
a transducer configured to be movable;
a cap including an operating portion configured to come in contact with an external subject and transmit an ultrasound signal generated by the transducer to the external subject and a cover portion extending from a lower portion of the operating portion;
a base frame connected to the cap so that an inner space of the cap is filled with oil; and
an impact mitigating member disposed entirely on the cap to protect the cap from an external impact,
wherein the impact mitigating member is disposed in the cover portion to prevent transmission of the ultrasound signal generated from the transducer from being interfered with by the impact mitigating member, and
a portion of the cap extends between the impact mitigating member and the base frame.

17. The ultrasonic probe of claim 16, wherein the impact mitigating member includes a first impact mitigating member having elasticity to mitigate an impact transmitted to the cap from outside.

18. The ultrasonic probe of claim 17, wherein the impact mitigating member further includes a second impact mitigating member configured to cover the first impact mitigating member to mitigate an impact transmitted to the cap from outside.

19. An ultrasonic probe comprising:
a transducer configured to be movable;
a cap including an upper cap configured to transmit the ultrasound signal generated by the transducer to outside and a lower cap disposed below the upper cap;
a base frame connected to the cap so that an inner space of the cap is filled with oil; and
an impact mitigating member disposed entirely on the cap and between the upper cap and the lower cap to protect the cap from an external impact,
wherein the lower cap extends between the impact mitigating member and the base frame.

20. The ultrasonic probe of claim 19, wherein the impact mitigating member includes:
a first impact mitigating member extending from the cap to connect the upper cap to the lower cap; and
a second impact mitigating member configured to cover the first impact mitigating member.

* * * * *